US009987064B2

(12) United States Patent
Jensen

(10) Patent No.: US 9,987,064 B2
(45) Date of Patent: Jun. 5, 2018

(54) ANTI-OVER TIGHTENING BONE SCREW FIXING ARRANGEMENT

(71) Applicant: FACET-LINK INC., Rockaway, NJ (US)

(72) Inventor: Harm-Iven Jensen, Noer (DE)

(73) Assignee: FACE-LINK INC., Rockaway, NJ (US)

( * ) Notice: Subject to any disclaimer, the term of this patent is extended or adjusted under 35 U.S.C. 154(b) by 385 days.

(21) Appl. No.: 14/435,102

(22) PCT Filed: Sep. 20, 2013

(86) PCT No.: PCT/EP2013/069584
§ 371 (c)(1),
(2) Date: Apr. 10, 2015

(87) PCT Pub. No.: WO2014/056704
PCT Pub. Date: Apr. 17, 2014

(65) Prior Publication Data
US 2015/0230845 A1     Aug. 20, 2015

(30) Foreign Application Priority Data
Oct. 10, 2012 (EP) .................... 12007011

(51) Int. Cl.
*A61B 17/80* (2006.01)
*A61B 17/86* (2006.01)
(52) U.S. Cl.
CPC ...... *A61B 17/8685* (2013.01); *A61B 17/8047* (2013.01); *A61B 2017/8655* (2013.01)
(58) Field of Classification Search
CPC ................................ A61B 17/8047
See application file for complete search history.

(56) References Cited

U.S. PATENT DOCUMENTS

2005/0154392 A1   7/2005   Medoff et al.
2007/0162016 A1*  7/2007   Matityahu .......... A61B 17/7059
                                                          606/281

(Continued)

FOREIGN PATENT DOCUMENTS

DE   10 2010 042 930     4/2012
WO   WO-2013/143558      10/2013

OTHER PUBLICATIONS

International Search Report and Written Opinion dated Oct. 24, 2013, directed to International Application No. PCT/EP2013/069584; 23 pages.

*Primary Examiner* — Olivia C Chang
(74) *Attorney, Agent, or Firm* — Morrison & Foerster LLP

(57) ABSTRACT

A fixing arrangement comprises a retaining element and a clamping sleeve which receives a bone screw. The bone screw has a head and a secondary thread and is pivotally mounted in the clamping sleeve. The clamping sleeve has a radially protruding section on the outer casing of the clamping sleeve and at least one track of a clamping thread, which complements the secondary thread, in the interior of the clamping sleeve. In the unclamped state, a free path is formed by a clearance on the clamping sleeve. A protruding section engages into an opening on the receiving seat in a formfitting manner, and the thickened section is shaped to expand towards the rear in the form of a cone. The cone angle is selected such that the free path divided by the tangent of the half-cone angle corresponds to 0.5 to 2.5 times the thread pitch of the secondary thread.

20 Claims, 3 Drawing Sheets

(56) References Cited

U.S. PATENT DOCUMENTS

| | | |
|---|---|---|
| 2008/0306550 A1 | 12/2008 | Matityahu |
| 2009/0012571 A1* | 1/2009 | Perrow .............. A61B 17/8047 606/280 |
| 2009/0062862 A1 | 3/2009 | Perrow et al. |
| 2010/0324604 A1 | 12/2010 | Mathieu et al. |
| 2014/0058457 A1* | 2/2014 | Appenzeller ........ A61B 17/864 606/304 |

* cited by examiner

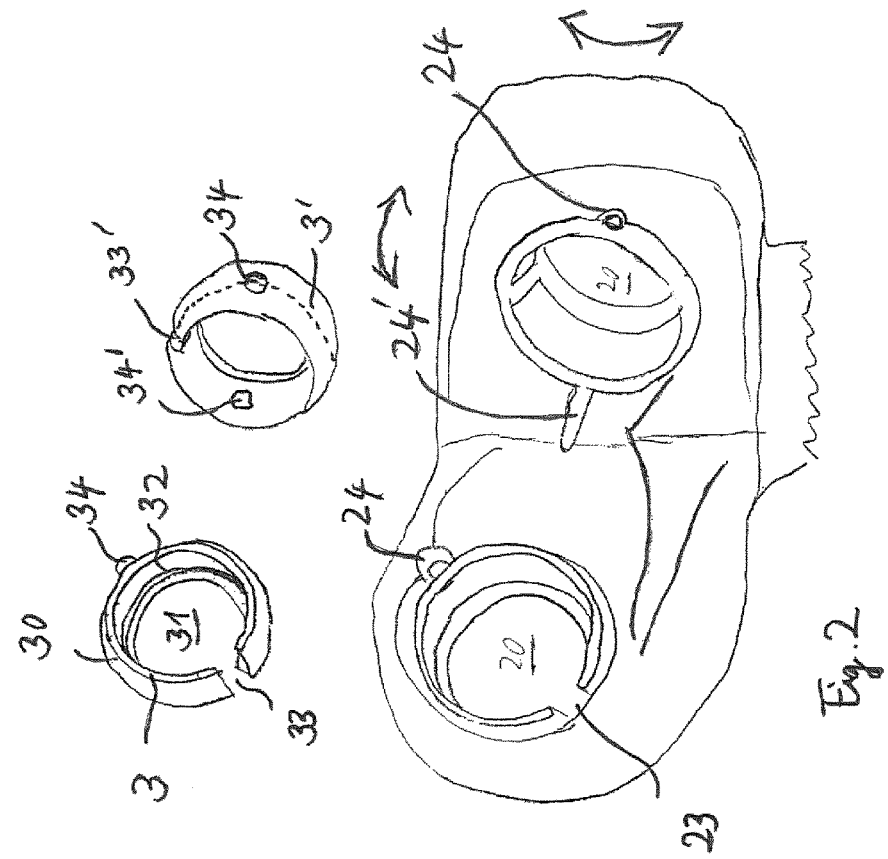
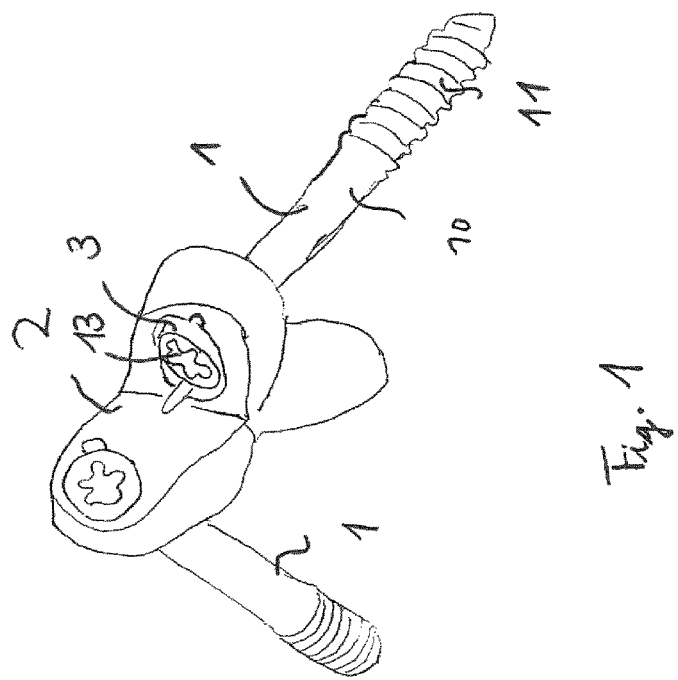
Fig. 2
Fig. 1

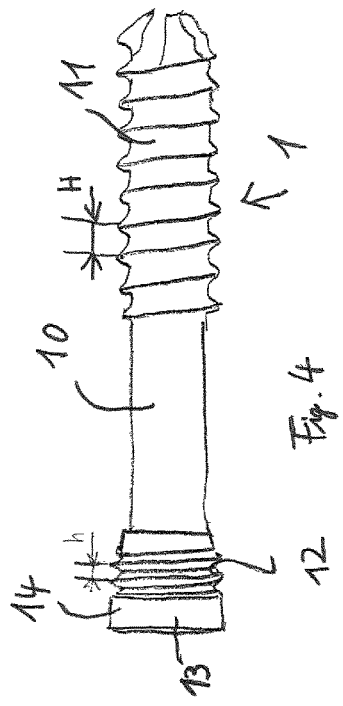
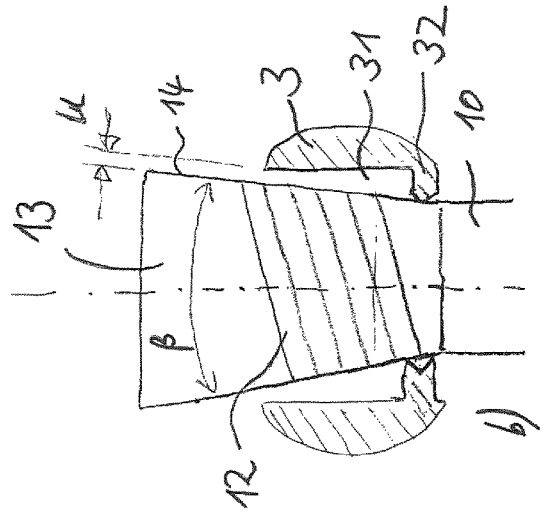
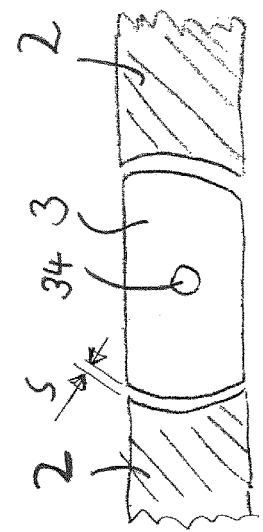
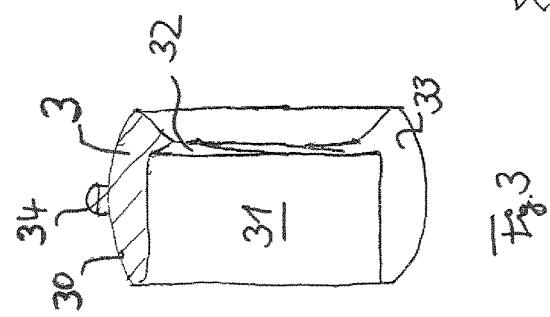

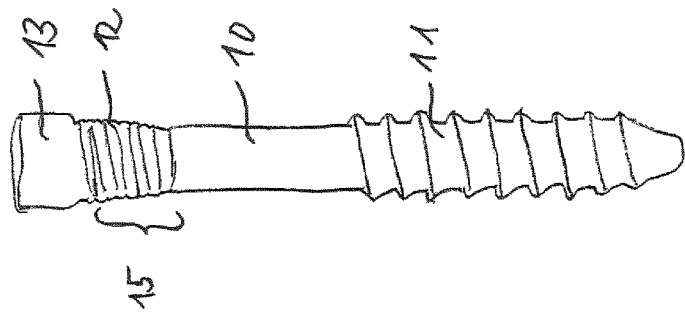
Fig. 7
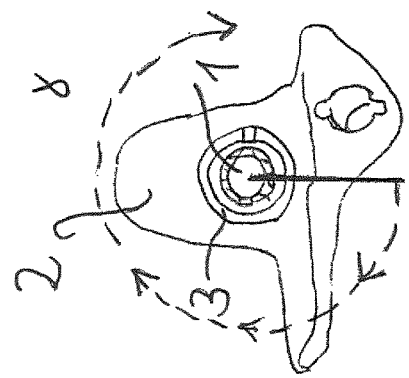
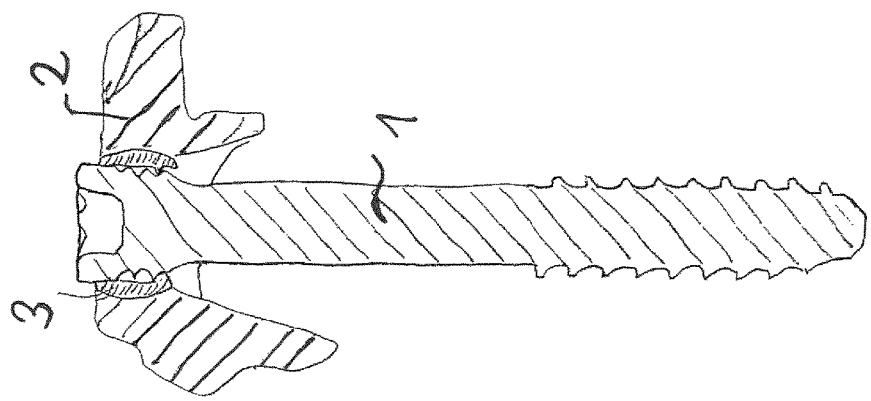
Fig. 6

ANTI-OVER TIGHTENING BONE SCREW FIXING ARRANGEMENT

REFERENCES TO RELATED APPLICATIONS

This application is a national stage application under 35 USC 371 of International Application No. PCT/EP2013/069584, filed Sep. 20, 2013, which claims priority to European Patent Application No. 12 007 011.5, filed Oct. 10, 2012, the entire contents of which are incorporated herein by reference.

FIELD OF THE INVENTION

The invention relates to a fixing arrangement comprising a holder without a bone screw for fastening purposes. The fixing arrangement serves in particular for connecting an implant to surrounding bone material.

BACKGROUND OF THE INVENTION

The use of bone screws for fastening implants in an adequately secure manner or for immobilizing joints is known. Depending on the application, positioning between the implant and the bone screw in an angularly rigid manner is sufficient in this connection, in other cases, an angularly variable (polyaxial) arrangement is necessary. To create such a possibility for angular adjustment, it is known to provide a dome-shaped clamping sleeve, which is mounted so as to be tiltable in a corresponding receiving seat in the holding body, between the object that is actually to be held (bone plate or implant) and the bone screw. For fastening, the bone screw is guided through an interior of the tiltable clamping sleeve, the thread of the bone screw engaging not only in the bone located below the holding body but also engaging in a corresponding counter thread on the inner wall of the clamping sleeve by way of its upper region close to the head. When the screw is fastened, not only is it consequently fastened to the bone, but the bone screw is forced onto the clamping sleeve opposite the holding body such that it is fixed in its angular position. In order to achieve the expanding effect necessary for the forcing action, the screw head is realized with oversize relative to the width of the interior. A fastening arrangement of this type is described in US 2005/154392 A1.

One difficulty when handling a fastening arrangement of this type is that the surgeon hardly gets any feeling of when the bone screw has been sufficiently tightened. Precisely for operations at places that are difficult to access or on small and therefore delicate bone parts, it is relatively unreliable to rely just on a feeling for the tightening torque. The use of a torque spanner for this does not create any kind of remedy as the tightening torque can vary considerably depending on the state of the thread (dry or moistened by bodily fluids). In addition, the tightening torque in the case of the afore-described fastening arrangement is further falsified as a result of additional force having to be applied for expanding the clamping sleeve.

SUMMARY OF THE INVENTION

Consequently, an object of the invention is to improve a fixing arrangement according to the preceding prior art to the effect that it is able to be tightened in a simpler manner at a reproducible strength.

This can be achieved by a fixing arrangement with the features as broadly described herein. Advantageous further developments are disclosed in the detailed embodiments below.

In the case of a fixing arrangement comprising a holder and a clamping sleeve which receives a bone screw, wherein the bone screw comprises a shank with a thread in the front region, a head and a thickening in the rear region, on which is arranged a secondary thread, and the holder is provided with a through-opening and a receiving seat in which the clamping sleeve is mounted so as to be pivotably movable, the clamping sleeve comprises on its outside surface a radially protruding projection and in its interior at least one thread of a clamping thread which is complementary to the secondary thread, wherein in the non-clamped state a free play is formed by a clearance on the clamping sleeve, it is provided according to the invention that the projection engages in a positive locking manner into a recess in the receiving seat, and the thickening is formed widening toward the rear in a cone-like manner, wherein the cone angle $\beta$ is chosen such that the free play divided by the tangent of half the cone angle ($\tan \beta/2$) corresponds to between 0.5 and 2.5 times the thread pitch of the secondary thread.

Some terms used are explained below:

The term "in a positive locking manner" is to be understood as the projection being guided in such a manner in the recess that the clamping sleeve is secured in a bidirectional manner, i.e. in opposite directions of rotation, against twisting with respect to the receiving seat. This means that the projection is secured in a clearance-free manner in the receiving seat apart from a slight clearance which is necessary for assembly.

With reference to the bone screw, the term "front" is to be understood as the direction to its tip on the end of the shank and the term "rear" is too understood as the opposite direction toward the head of the bone screw.

The term "pivotally movable" is to be understood as the axis of the bone screw, which is fixed by means of the clamping sleeve, being able to assume a freely adjustable angle in the holder with reference to a center axis of the through-passage. The adjustment range is preferably at least 15° in each direction and in the center axis of the through-opening.

An aspect of the invention is the concept of creating a precise definition of the tightening path until a secure seat is achieved as a result of combining two measures. A first aspect of said combination is that the clamping sleeve is anchored in a non-rotatable manner in relation to the holder by means of the projection. In addition, the clamping sleeve in the initial state (bone screw mounted, but not yet tightened) comprises a clearance to its receiving seat and/or to the bone screw, said clearance which is designated as free play disappearing gradually when the bone screw is tightened as a result of the conical development of the thickening of the bone screw. The rate at which the free play disappears depends on the angle of twist of the bone screw and the pitch of the secondary thread on the thickening. In this connection, the feed path achieved by the twisting of the bone screw and the expansion path achieved by the conical development of the thickening, insofar as it results finally in the disappearing of the clearance, are not identical, but are related to one another by the cone angle $\beta$. The inventor has recognized that by said cone angle not being chosen arbitrarily, but in a specific manner, a definition of the tightening angle of the screw up to the disappearing of the free play can be achieved when—and this is a second aspect of the invention—the clamping sleeve is itself secured non-rotatably in a bidirectional manner in the receiving seat. For without the bidirectional, non-rotatable securement, there would be no fixed reference system such that the tightening angle could not be specified in a meaningful manner if the clamping sleeve were namely entrained in rotation. As in practical use, it is within the bounds of possibility for a surgeon sometimes to loosen a screw, for example in order to apply a torque spanner again, the bidirectional fixing has enormously important implications in practice. The inventor is credited with having recognized that the determining of the cone angle in the afore-described manner has mandatorily to be combined with the fixing of the clamping sleeve in a bidirectionally non-rotatable manner in order to achieve reliable handling in practice and consequently a fixing arrangement that is suitable for practical application.

The clearance forming the free play can be formed in different ways. In an expedient manner, this is a clearance between the clamping sleeve and the receiving seat, an outer clearance of the clamping sleeve as it were. In addition to this or as an alternative to it, the free play can also be formed by an undersize of the thickening of the bone screw with reference to the width of the interior of the clamping sleeve, that is an inner clearance. It is also possible to combine the two. Consequently, practicable, relatively large tightening angles of preferably at least 270° corresponding to a ¾ turn can be achieved.

In addition, elasticities of the bone screw, of the holder and in particular of the clamping sleeve can also be taken into consideration in the free play. For example, if the material used for the bone screw is so elastic that the thickening is compressed under load, the compression section would have to be taken into consideration additionally for the free play. However, this is not essential as the materials used for many practical applications can be seen as sufficiently rigid.

In an expedient manner, the thickening and the head of the screw are combined together. This enables the bone screw to be developed in a structurally simple manner. However, the combination is not compulsory.

The invention has proved its worth in particular in the case of embodiments where the secondary thread and the thread on the shank of the bone screw have different pitches. The thread of the bone screw, as a rule, is relatively coarse (pitch within the range of between 1.25 to 2.5 mm), whilst a fine thread is preferred for the secondary thread. Thanks to the difference in pitch, the two threads can be optimized in this way to their respective intended applications, namely anchoring in the bone material on the one hand or interacting with the clamping sleeve which is produced in the majority of cases from metal on the other hand. The pitches of the threads are preferably chosen such that the secondary thread comprises a smaller pitch than the pitch of the thread on the shank of the bone screw, preferably between 0.4 and 0.7 times smaller. As a result of the difference in pitch, when the bone screw is tightened the fragments which are connected by the bone screw are pulled toward one another. A defined tensioning of the two bone fragments consequently results from limiting the tightening angle according to the invention. The danger of over-tightening with the risk of tearing the bone screw out of the thread is consequently successfully countered.

In an expedient manner, the pitch of the clamping thread in the interior of the clamping sleeve is limited to preferably no more than three threads, further preferably to no more than one and half threads. With such a development it is particularly simple to guide the front thread of the bone screw through the thread on the inside surface of the interior of the clamping sleeve, even if it comprises a different pitch but the same diameter as the clamping thread.

The clamping thread is expediently realized such that its interior is cylindrical. This not only simplifies the production, but also offers the advantage of the cone angle, which is determining for calculating the tightening path, being determined just by the thickening of the bone screw. On the other hand, however, developing the interior in a conical manner and realizing in contrast the outside surface of the thickening in a cylindrical manner should not be ruled out either.

In an advantageous manner, the clamping sleeve and the receiving seat are formed in such a manner that a boundary face between them is sphere-like. It is particularly expedient when an outside surface of the clamping sleeve is formed in a spherical manner. This produces a particularly favorable development for a large pivot angle of the clamping sleeve in its receiving seat.

The clamping sleeve is preferably slotted once. This means that a continuous slot which extends over the entire height of the clamping sleeve is provided. This produces good expandability, but also better compressability for simplifying assembly.

In an advantageous manner, the projection is arranged on the clamping sleeve in the region of the greatest width (equator) of the clamping sleeve. This produces favorable tilt characteristics independent of the direction of the tilt angle. In addition, the projection is expediently realized so as to be rotationally symmetrical. This promotes the uniformity of the tilt characteristics independently of the direction of the tilt angle. In addition, said development of the projection has the advantage of avoiding the clamping sleeve wobbling in its receiving seat during movement. Particularly expedient for this, the tip of the projection is in a dome-shaped, in particular semi-spherical form. The projection can comprise a column-like, in particular cylindrical substructure. However, this should preferably be small in height (less that the width of the projection) in order to counter the risk of wobbling.

It is particularly expedient to realize the recess which receives in the projection in a slot-like manner in the receiving seat, the slot-like recess extending in the direction of the center axis of the through-opening. Consequently, the clamping sleeve can be mounted in a simple manner by being pushed into its position in the receiving seat. At the same time, it is secured there in a positive locking manner practically without any clearance. Simple mountability is combined with reliable, bidirectionally non-rotatable securing in this manner.

It has proven particularly worthwhile to arrange a second projection diametrically opposite on the clamping sleeve, with a corresponding second recess to be provided on the receiving seat. This secures the clamping sleeve in a particularly reliable manner, the tilt axis of the clamping sleeve being precisely defined as a result of the two projections.

The slot-like form of the recess further provides the advantage that the projection moves up and down therein such that a second tilt movement about an axis orthogonally with respect to the aforementioned tilt axis is made possible. The freedom of movement of the clamping sleeve and consequently the polyaxiality of the fastening of the bone screw is consequently increased.

BRIEF DESCRIPTION OF THE DRAWINGS

The invention is explained in more detail below with reference to the accompanying drawings, in which an advantageous exemplary embodiment is shown, and in which:

FIG. 1 shows an overview of the fixing arrangement according to an exemplary embodiment of the invention, in the mounted state;

FIG. 2 shows a partly enlarged detail from FIG. 1;

FIG. 3 shows a sectional view of a clamping sleeve;

FIG. 4 shows a sectional view of a bone screw;

FIGS. 5a, b show schematic representations of the free play and the cone angle;

FIG. 6 shows an assembly drawing with the tightening angle represented; and

FIG. 7 shows and alternative embodiment of the bone screw.

DETAILED DESCRIPTION OF THE INVENTION

A fixing arrangement according to the invention includes a bone screw 1, a holder 2 and a clamping sleeve 3. The exemplary embodiment shown in the figures provides a double holder which includes two bone screws 1 and two clamping sleeves 3.

A fixing arrangement of this type with two bone screws 1 can be realized, for example, as an externally bridging implant for strengthening a lamina of a vertebra (not shown), in particular after a partial resection of the lamina. Such an implant is the object of a further application by the same applicant, given the international reference PCT/EP2012/001357.

The bone screw 1 is realized in a conventional manner per se, having a shank 10 in the front region of which a bone thread 11 is provided. The bone thread 11 can also extend over the entire shank 10. A screw head 13, which is realized as a thickening, is provided on the rear end of the shank 10. It is provided on its outer end face with a star-shaped indentation for receiving a correspondingly realized screwdriver (not shown). The screw head 13 is shaped in a conical manner and comprises on its outside surface 14 a cone angle β. A secondary thread 12 is arranged on the outside surface 14. It is realized with the same directional orientation as the bone thread 11, but comprises a considerably smaller pitch h (only half of the pitch H of the bone thread 11 in the exemplary embodiment shown). The secondary thread 12 extends approximately over three threads. The thickening 15 can also be realized separately from the screw head 13 (see FIG. 7).

At its two ends, the holder 2 comprises a through-passage 20 each for receiving one of the bone screws 1. It is widened in a spherical segment-shaped manner in its central region and consequently forms a receiving seat 23 for the clamping sleeve 3. A slot-like recess 24, which extends at least over half the depth of the through-passage 20, is formed on one side of the receiving seat 23. The receiving seat 23 serves for securing the clamping sleeve 3 in a pivotally movable manner. To this end, the clamping sleeve 3 comprises a spherical outside surface 30, the contour of which is substantially complementary to that of the receiving seat 23. The clamping sleeve 3 comprises a central opening which forms a cylindrical interior 31. The bone screw 1 is pushed through said cylindrical interior in the mounted state. In this case, the bone screw 1 meshes with one and a half times a thread of a clamping thread 32 which is arranged on the wall of the interior 31 and is complementary to the secondary thread 12 of the bone screw 1.

The clamping screw 3 further comprises a continuous slot 33 on one side. A radially outwardly projecting projection 34 is arranged opposite on the equator 35 on the outside surface 31 of the clamping sleeve 3. The projection 34 in the exemplary embodiment shown is formed in a semi-spherical manner. Its dimensions are chosen so as to match those of the slot-like recess 24 such that the projection 34 can be inserted in a positive locking manner in the slot-like recess 24 with a small amount of clearance (small within the meaning of this application is to be understood as a clearance of approximately between 5% and 30% of the width of the projection). In the mounted state, the clamping sleeve 3 is thus secured in a bidirectional manner against twisting relative to the holder 2. In conjunction with the slot-like recess 24, the semi-spherical development of the projection 34 allows for a double cardanic bearing arrangement of the clamping sleeve 3 in the holder 2, as is visualized in FIG. 2 by the two arrows in the right-hand half of the figure. Consequently, the bone screw 1 has an axis-variable (polyaxial) bearing arrangement in the holder 2. In practice, an angular adjustment range of approximately 15 degrees in each direction is made possible.

Reference is now made to the sectional representations in FIGS. 5a and 5b. For practical reasons of easy mountability and better pivotability, in the initial state the clamping sleeve 3 sits with clearance in its receiving seat 23. This means that the inside diameter of the spherical segment-shaped receiving seat 23 is greater than the outside diameter of the spherical outside surface 30 of the clamping sleeve 3.

In addition, in the exemplary embodiment shown the bone screw 1 comprises an undersize U in the region of the conical thickening, here the screw head 13. The undersize U is defined as the gap between the cone outside surface 14 and the edge of the interior 31 in the state when the bone screw 1 grips the clamping thread by way of its secondary thread 12 (see FIG. 5b).

Consequently, a free play F, which is determined by the sum of the clearance S and the undersize U, is produced overall by the clearance S and the undersize F according to the equation $$F=S+U.$$

Said free play F is gradually reduced when the bone screw 1 is tightened on account of the conical widening of the screw head 13. When it has disappeared altogether, the bone screw 1 is tightened. Further tightening could then result in overloading the screw connection, in particular to the bone thread 11 being undesirably torn out of the vertebral body.

In order to prevent this in a reliable manner, a certain tightening angle γ is defined which the surgeon has to apply for tightening. It can be, for example, approximately 270 degrees, that is a three-quarter turn (see FIG. 6). The starting point for this is the position where the bone screw just engages into the clamping thread 32 by way of its secondary thread 12 (see FIG. 5b). Such a measurement of 270 degrees (corresponding to a three-quarter turn) provides a good compromise for practical applicability between good adjustability on the one hand and error-free operation on the other hand. In order then to achieve that the free play F is used up after a three-quarter turn, the cone angle β has to be chosen in a corresponding manner. According to the invention, this is effected according to the equation $$F/\tan(\beta/2)=270°/360°*h,$$

wherein h is the pitch of the secondary thread 12. To calculate the wanted cone angle β, the equation can be converted to $$\beta=2*\arctan(F/(0.75*h)).$$

The aforementioned calculation instruction for the cone angle β applies irrespective of whether the free play F is formed just by the clearance S or the undersize U or by a combination of the two.

The definition of the tightening angle, here in the example 270 degrees for a three-quarter turn, is, however, meaningless if the clamping sleeve has not been secured against twisting. For without an anti-twist means, the clamping sleeve can be entrained in rotation, as a result of which the definition of the tightening angle loses its basis. The invention counters this danger by securing the clamping sleeve 3 in the slot-like recess 24 non-rotatably by means of the projection 34, in a bidirectional manner. Only then is the definition of a tightening angle feasible in practice. As the clamping sleeve 3 is held in a non-rotatable manner on the holder 2, the reference point for the tightening angle remains constant. This applies even if the screw is loosened, which is not provided for per se but is, however, not unusual, for example when the screwdriver is implemented. The concept of the tightening angle only obtains practical usefulness in an operating environment in combination with said bidirectionally acting mounting of the clamping sleeve 3.

When the bone screw 1 is tightened by the specific tightening angle γ, a double effect is obtained. On the one hand, the clamping sleeve 3 is reliably tensioned against the holder 2 and the axis of the bone screw 1 is consequently secured. On the other hand, the bone screw 1 is now tightened sufficiently for a reliable fastening in the vertebra, but is not tightened too much such that the vertebra cannot be damaged on account of the bone thread being torn out of the vertebra due to over-tightening. If the bone screw 1 joins two bone fragments, they are pulled toward one another at a well-defined tension.

Therefore, reliable tightening is combined with practicable over-tightening protection.

In the case of an alternative embodiment, as is shown in FIG. 2 on the right-hand half of the figure, it can be provided that two projections 34, 34' are arranged on a clamping sleeve 3'. A second projection 34' which is realized in an identical manner to the projection 34 is provided for this purpose. It is arranged diametrically opposite said projection on the outside surface of the clamping sleeve 3, but points in the opposite direction. In this case the slot 33' is arranged at a position between the two projections 34, 34' on the clamping sleeve 3, preferably in a cross position. The receiving seat 23 is provided with a corresponding second slot-like recess 24' on the holder 2. A second tilt axis is defined by way of the double projections 34, 34' such that the clamping sleeve 3 is movable in a reliably guided double cardanic manner in the holder 2.

The invention claimed is:

1. A fixing arrangement comprising a holder, a clamping sleeve, and a bone screw received in the clamping sleeve, wherein the bone screw comprises a shank with a front thread and a thickening with a secondary thread at a head end of the bone screw, wherein the holder is provided with a through-opening and a receiving seat in which the clamping sleeve is mounted so as to be pivotably movable, wherein the clamping sleeve comprises on an outside surface of the clamping sleeve a radially protruding projection and in an interior of the clamping sleeve at least one thread of a clamping thread which is complementary to the secondary thread, wherein prior to tightening of the bone screw a free play is formed by a sum of a clearance between the clamping sleeve and the receiving seat and an undersize formed by a gap between the thickening and the interior of the clamping sleeve, wherein the projection engages in a positive locking manner into a recess on the receiving seat, wherein the thickening widens toward the head end of the bone screw in a cone-like manner, and wherein the cone angle is chosen such that the free play divided by the tangent of half the cone angle is between 0.5 and 2.5 times the thread pitch of the secondary thread.

2. The fixing arrangement of claim 1, wherein the thickening is part of a head of the bone screw.

3. The fixing arrangement of claim 1, wherein the secondary thread and the front thread on the shank of the bone screw have different pitches.

4. The fixing arrangement of claim 3, wherein the secondary thread comprises a smaller pitch than the front end.

5. The fixing arrangement of claim 1, wherein the interior of the clamping sleeve is cylindrical.

6. The fixing arrangement of claim 1, wherein the interior of the clamping sleeve is conical and the outside surface of the thickening is cylindrical.

7. The fixing arrangement of claim 1, wherein the pitch of the clamping thread is a maximum of three times the pitch of the front thread on the shank of the screw.

8. The fixing arrangement of claim 1, wherein the outside surface of the clamping sleeve is formed in a spherical manner and a boundary face between the clamping sleeve and the receiving seat is sphere-like.

9. The fixing arrangement claim 1, wherein the clamping sleeve is slotted once.

10. The fixing arrangement of claim 1, wherein the projection is arranged in a region of greatest width of the outside surface of the clamping sleeve.

11. The fixing arrangement of claim 1, wherein the projection is rotationally symmetrical.

12. The fixing arrangement of claim 11, wherein the projection comprises a dome-shaped tip.

13. The fixing arrangement of claim 11, wherein the projection comprises a column-like substructure.

14. The fixing arrangement of claim 1, wherein the recess in the receiving seat is slot-like and extends in the direction of a center axis of the through-passage.

15. The fixing arrangement of claim 1, wherein a second projection is arranged diametrically opposite the projection, wherein a corresponding second recess is provided in the receiving seat.

16. The fixing arrangement of claim 4, wherein the smaller pitch is between 0.4 and 0.7 times smaller than the pitch of the front thread.

17. The fixing arrangement of claim 1, wherein the pitch of the clamping thread is one and a half times the pitch of the front thread on the shank of the screw.

18. The fixing arrangement of claim 10, wherein the region of greatest width of the clamping sleeve is on an equator thereof.

19. The fixing arrangement of claim 1, wherein the projection comprises a semi-spherical tip.

20. The fixing arrangement of claim 1, wherein the projection comprises a cylindrical substructure.

* * * * *

UNITED STATES PATENT AND TRADEMARK OFFICE
CERTIFICATE OF CORRECTION

PATENT NO. : 9,987,064 B2  
APPLICATION NO. : 14/435102  
DATED : June 5, 2018  
INVENTOR(S) : Harm-Iven Jensen Page 1 of 1

It is certified that error appears in the above-identified patent and that said Letters Patent is hereby corrected as shown below:

On the Title Page

Item (73) at Column 1, Name of Assignee, please delete "FACE-LINK" and insert --FACET-LINK--.

In the Specification

At Column 4, Line number 22, please delete "compressability" and insert --compressibility--.

In the Claims

At Column 8, Claim number 4, Line number 18, please delete "end." and insert --thread.--.

At Column 8, Claim number 9, Line number 31, please delete "claim" and insert --of claim--.

Signed and Sealed this  
Twenty-first Day of August, 2018

Andrei Iancu  
*Director of the United States Patent and Trademark Office*